United States Patent [19]

Onishi et al.

[11] Patent Number: 6,114,282
[45] Date of Patent: Sep. 5, 2000

[54] THERMAL RECORDING MATERIAL AND NOVEL CRYSTAL OF BISPHENOL S DERIVATIVE

[75] Inventors: Masao Onishi, Saitama; Masaaki Saito; Hirofumi Iwamoto, both of Hiroshima, all of Japan

[73] Assignee: Nippon Kayaku Kabushiki Kaisha, Tokyo, Japan

[21] Appl. No.: 09/214,795

[22] PCT Filed: May 13, 1998

[86] PCT No.: PCT/JP98/02103

§ 371 Date: Jan. 11, 1999

§ 102(e) Date: Jan. 11, 1999

[87] PCT Pub. No.: WO98/51511

PCT Pub. Date: Nov. 19, 1998

[30] Foreign Application Priority Data

| May 14, 1997 | [JP] | Japan | 9-138011 |
| May 14, 1997 | [JP] | Japan | 9-138012 |
| May 14, 1997 | [JP] | Japan | 9-138013 |

[51] Int. Cl.[7] .................................................. B41M 5/30
[52] U.S. Cl. ........................ 503/216; 427/150; 568/28; 568/32; 568/33; 568/34
[58] Field of Search .................... 427/150–152; 503/216, 225; 568/28, 32–34

[56] References Cited

FOREIGN PATENT DOCUMENTS

| 60-208286 | 10/1985 | Japan . |
| 61-89090 | 5/1986 | Japan . |
| 61-199985 | 9/1986 | Japan . |
| 61-199986 | 9/1986 | Japan . |
| 61-199987 | 9/1986 | Japan . |
| 61-199988 | 9/1986 | Japan . |
| 61-228985 | 10/1986 | Japan . |
| 62-53957 | 3/1987 | Japan . |
| 63-3988 | 1/1988 | Japan . |
| 1-67380 | 3/1989 | Japan . |
| 1-150576 | 6/1989 | Japan . |
| 1-178491 | 7/1989 | Japan . |
| 2-282343 | 11/1990 | Japan . |
| 5-301854 | 11/1993 | Japan . |
| 6-107623 | 4/1994 | Japan . |
| 6-143826 | 5/1994 | Japan . |

OTHER PUBLICATIONS

Copy of the International Search Report dated Aug. 11, 1998.

J. Indian Chem. Soc., vol. LIV, No. 10. pp. 931–1014; Oct. 1977; "Journal of the Indian Chemical Society".

*Primary Examiner*—Bruce H. Hess
*Attorney, Agent, or Firm*—Nields, Lemack & Dingman

[57] ABSTRACT

A heat-sensitive recording material in which a heat-sensitive color-developing layer comprising, as the main components, a usually colorless or light-colored color former and a developer capable of developing the color former upon heating on a support, characterized by comprising, as the developer, crystals of 3,3'-diallyl-4,4'-dihydroxy-diphenyl sulfone which have DSC (Te) of at least 149° C. and which are of a crystal form characterized by an X-ray diffraction pattern having peaks at least at diffraction angles (2θ) [°] of 7.2 and 22.0, obtained by an X-ray powder diffractometry using Cu—Kα rays. This heat-sensitive recording material is high in sensitivity, little in Discoloration of the ground in heat and moisture and excellent in image durability.

14 Claims, 2 Drawing Sheets

THERMAL RECORDING MATERIAL AND NOVEL CRYSTAL OF BISPHENOL S DERIVATIVE

TECHNICAL FIELD

This invention relates to a novel crystal of a bisphenol S derivative and a heat-sensitive recording material using the same which material is high in sensitivity, little in Discoloration of the ground (darkening of undeveloped portion) and excellent in image durability.

BACKGROUND ART

A heat-sensitive recording material is generally one obtained by separately dispersing a colorless or light color leuco-dye and a developer such as a phenolic material or the like in the form of fine particles, then mixing the two, adding thereto additives such as a binder, a sensitizer, a filler, a lubricant and the like to form a coating solution and then applying the coating solution to paper, a film, a synthetic paper or the like, and one or both of the leuco-dye and the developer are melted by heating and the two are contacted to cause a chemical reaction, thereby obtaining a developed record. For developing this heat-sensitive recording sheet, a thermal printer or the like having a built-in thermal head is used. This heat-sensitive recording method has such characteristics that as compared with other recording methods, (1) no noise is caused during recording, (2) development, fixing and the like are not required, (3) maintenance is unnecessary, (4) the machine is relatively inexpensive and the like, and hence, is widely used in the facsimile field, the field of printer for computer output, electronic calculator and the like, the field of recorder for medical measurement, the automatic ticket vending machine field, the heat-sensitive recording type label field and the like.

Recently, with the POS systemization in a retail store, a supermarket and the like and the automatization of the system of traffic facilities, the application of heat-sensitive recording materials to labels, tickets, coupon tickets and the like increases. In these applications, it has been desired that the heat-sensitive recording material has a much more improved preservation stability. In addition, a demand for high speed recording has become higher and the development of a heat-sensitive recording material capable of sufficiently responding to the high speed recording has been strongly desired. However, in general, when the sensitivity of a heat-sensitive recording material is heightened to make the heat-responsibility good, such a disadvantage that Discoloration of the ground is caused becomes easy to cause. As to heat-sensitive recording materials in which 3,3'-diallyl-4,4'-dihydroxydiphenyl sulfone which is an example of the bisphenol S derivative is used as a developer, many patents have been applied for. They include, for example, JP-A-60-208,286, JP-A-61-89,090, JP-A-61-199,985, JP-A-61-199,986, JP-A-61-199,987, JP-A-61-199,988, JP-A-61-228,985, JP-A-62-53,957, JP-A-63-3,988, JP-A-1-67,380, JP-A-1-150,576, JP-A-1-178,491 and the like. Among them, those describing a method for preparing 3,3'-diallyl-4,4'-dihydroxydiphenyl sulfone are two of JP-A-61-89,090 and JP-A-62-53,957. However, even when 3,3'-diallyl-4,4'-dihydroxydiphenyl sulfone prepared according to the methods described therein is used, the recent high requirement for the Discoloration of the ground in heat and moisture has not been satisfied though the enhancement of preservation stability is improved to some extent.

DISCLOSURE OF THE INVENTION

The object of this invention is to overcome the above-mentioned disadvantage of the prior art and to provide a heat-sensitive recording material which is high in sensitivity and little in Discoloration of the ground in heat and moisture and gives an excellent image.

The present inventors have repeated various examinations in order to achieve the above-mentioned object and have consequently found that a heat-sensitive recording material which is high in sensitivity and excellent in image durability and has been greatly improved in Discoloration of the ground in heat and moisture is obtained by using, as a developer, crystals of the specific 3,3'-diallyl-4,4'-dihydroxydiphenyl sulfone mentioned in the item (1) mentioned blow, whereby this invention has been completed. That is to say, this invention relates to:

(1) a heat-sensitive recording material which has, on a support, a heat-sensitive color-developing layer comprising a usually colorless or light-colored color former and a developer capable of developing the color former upon heating, characterized by containing, as the developer, crystals of 3,3'-diallyl-4,41-dihydroxydiphenyl sulfone which have DSC (Te) of at least 149° C. and are of a crystal form characterized by an X-ray diffraction pattern having at least peaks at diffraction angles (2θ) [°] of 7.2 and 22.0 obtained by an X-ray powder diffractometry using Cu—Kα rays;

(2) the heat-sensitive recording material according to the item (1), wherein the DSC (Te) of the crystal of 3,3'-diallyl-4,4'-dihydroxydiphenyl sulfone is at least 151.50° C.;

(3) the heat-sensitive recording material according to the item (1), wherein the crystal of 3,3'-diallyl-4,4'-dihydroxydiphenyl sulfone is of a crystal form characterized by an X-ray diffraction pattern having, in addition to the peaks at diffraction angles (2θ) [0] of 7.2 and 22.0, relatively strong peaks at 14.5, 16.3, 18.0, 20.0, 21.0, 24.7 and 29.0, obtained by an X-ray powder diffractometry using Cu—Kα rays;

(4) the heat-sensitive recording material according to the item (1), wherein the 3,3'-diallyl-4,4'-dihydroxydiphenyl sulfone content in the crystals of 3,3'-diallyl-4,4'-dihydroxydiphenyl sulfone is at least 95%;

(5) the heat-sensitive recording material according to the item (1), wherein the 3,3'-diallyl-4,4'-dihydroxydiphenyl sulfone content in the crystals of 3,3'-diallyl-4,4'-dihydroxydiphenyl sulfone is at least 95.5%;

(6) the heat-sensitive recording material according to the item (1), wherein the total of the three contents of 3-allyl-4,4'-dihydroxydiphenyl sulfone, 5-(3-allyl-4-hydroxy)phenyl sulfone-1-oxa-2-methylindane and 3-allyl-4'-allyloxy-4-hydroxydiphenyl sulfone in the crystals of 3,3'-diallyl-4,4'-dihydroxydiphenyl sulfone is not more than 3%;

(7) the heat-sensitive recording material according to the item (6), wherein the 3-allyl-4,4'-dihydroxydiphenyl sulfone content in the crystals of 3,3'-diallyl-4,4'-dihydroxydiphenyl sulfone is not more than 2%;

(8) the heat-sensitive recording material according to the item (1), wherein the total of the three contents of 3-allyl-4,4'-dihydroxydiphenyl sulfone, 5-(3-allyl-4-hydroxy)phenyl sulfone-1-oxa-2-methylindane and 3-allyl-4'-allyloxy-4-hydroxydiphenyl sulfone in the crystals of 3,3'-diallyl-4,4'-dihydroxydiphenyl sulfone is not more than 2%;

(9) a heat-sensitive recording material in which a heat-sensitive color-developing layer comprising, as the main components, a usually colorless or light-colored color former and a developrt capable of developing the above color former upon heating is provided on a support, characterized by containing, as the developer, crystals of 3,3'-diallyl-4,4'-dihydroxydiphenyl sulfone having the following features (a) to (e):

(a) the DSC (Te) is at least 149° C.,
(b) the crystal is of a crystal form characterized by an X-ray diffraction pattern having peaks at diffraction angles (2θ) [°] of 7.2 and 22.0, obtained by an X-ray powder diffractometry using Cu—Kα rays,
(c) the 3,3'-diallyl-4,4'-dihydroxydiphenyl sulfone content is at least 95.5%,
(d) the total of the three contents of 3-allyl-4,4'-dihydroxydiphenyl sulfone, 5-(3-allyl-4-hydroxy)phenyl sulfone-1-oxa-2-methylindane and 3-allyl-4'-allyloxy-4-hydroxydiphenyl sulfone is not more than 3%, and
(e) the 3-allyl-4,4'-dihydroxydiphenyl sulfone content is not more than 2%, the 5-(3-allyl-4-hydroxy)phenyl sulfone-1-oxa-2-methylindane content is not more than 2% and the 3-allyl-4'-allyloxy-4-hydroxydiphenyl sulfone content is not more than 2%;

(10) a heat-sensitive recording material which has, on a support, a heat-sensitive color-developing layer comprising a usually colorless or light-colored color former and a developer capable of developing the above color former upon heating, characterized by containing, as the developer, crystals of 3,3'-diallyl-4,4'-dihydroxydiphenyl sulfone having the following features (f) to (j):

(f) the DSC (Te) is at least 151.5° C.,
(g) the crystal is of a crystal form characterized by an X-ray diffraction pattern having, in addition to peaks at diffraction angles (2θ) [°] of 7.2 and 22.0, peaks at 14.5, 16.3, 18.0, 20.0, 21.0, 24.7 and 29.0, obtained by an X-ray powder diffractometry using Cu—Kα rays,
(h) the 3,3'-diallyl-4,41-dihydroxydiphenyl sulfone content is at least 96%,
(i) the total of the three contents of 3-allyl-4,4'-dihydroxydiphenyl sulfone, 5-(3-allyl-4-hydroxy)phenyl sulfone-1-oxa-2-methylindane and 3-allyl-4'-allyloxy-4-hydroxydiphenyl sulfone is not more than 2%, and
(j) the 3-allyl-4,4'-dihydroxydiphenyl sulfone content is not more than 2%, the 5-(3-allyl-4-hydroxy)phenyl sulfone-1-oxa-2-methylindane content is not more than 1% and the 3-allyl-4'-allyloxy-4-hydroxydiphenyl sulfone content is not more than 1%;

(11) a crystal of 3,3'-diallyl-4,4'-dihydroxydiphenyl sulfone which has DSC (Te) of at least 149° C. and has a crystal form characterized by an X-ray diffraction pattern having peaks at diffraction angles (2θ) [0] of 7.2 and 22.0 obtained by an X-ray powder diffractometry using Cu—Kα rays;

(12) the crystal of 3,3'-diallyl-4,4'-dihydroxydiphenyl sulfone according to the item (11), wherein the 3,3'-diallyl-4,4'-dihydroxydiphenyl sulfone content is at least 95.5%, and the total of the three contents of 3-allyl-4,4'-dihydroxydiphenyl sulfone, 5-(3-allyl-4-hydroxy)phenyl sulfone-1-oxa-2-methylindane and 3-allyl-4'-allyloxy-4-hydroxydiphenyl sulfone is not more than 3%;

(13) the crystal of 3,3'-diallyl-4,4'-dihydroxydiphenyl sulfone according to the item (12), wherein the 3-allyl-4,4'-dihydroxydiphenyl sulfone content is not more than 2%, the 5-(3-allyl-4-hydroxy)phenyl sulfone-1-oxa-2-hydroxydiphenyl sulfone content is not more than 2% and the 3-allyl-4'-allyloxy-4-hydroxydiphenyl sulfone content is not more than 2%; and

(14) the crystal of 3,3'-diallyl-4,4'-dihydroxydiphenyl sulfone according to the item (12), wherein the 3-allyl-4,4'-dihydroxydiphenyl sulfone content is not more than 2%, the 5-(3-allyl-4-hydroxy)phenyl sulfone-1-oxa-2-methylindane content is not more than 1%, the 3-allyl-4'-allyloxy-4-hydroxydiphenyl sulfone content is not more than 1% and the total of the three contents is not more than 2%.

Figure 1:
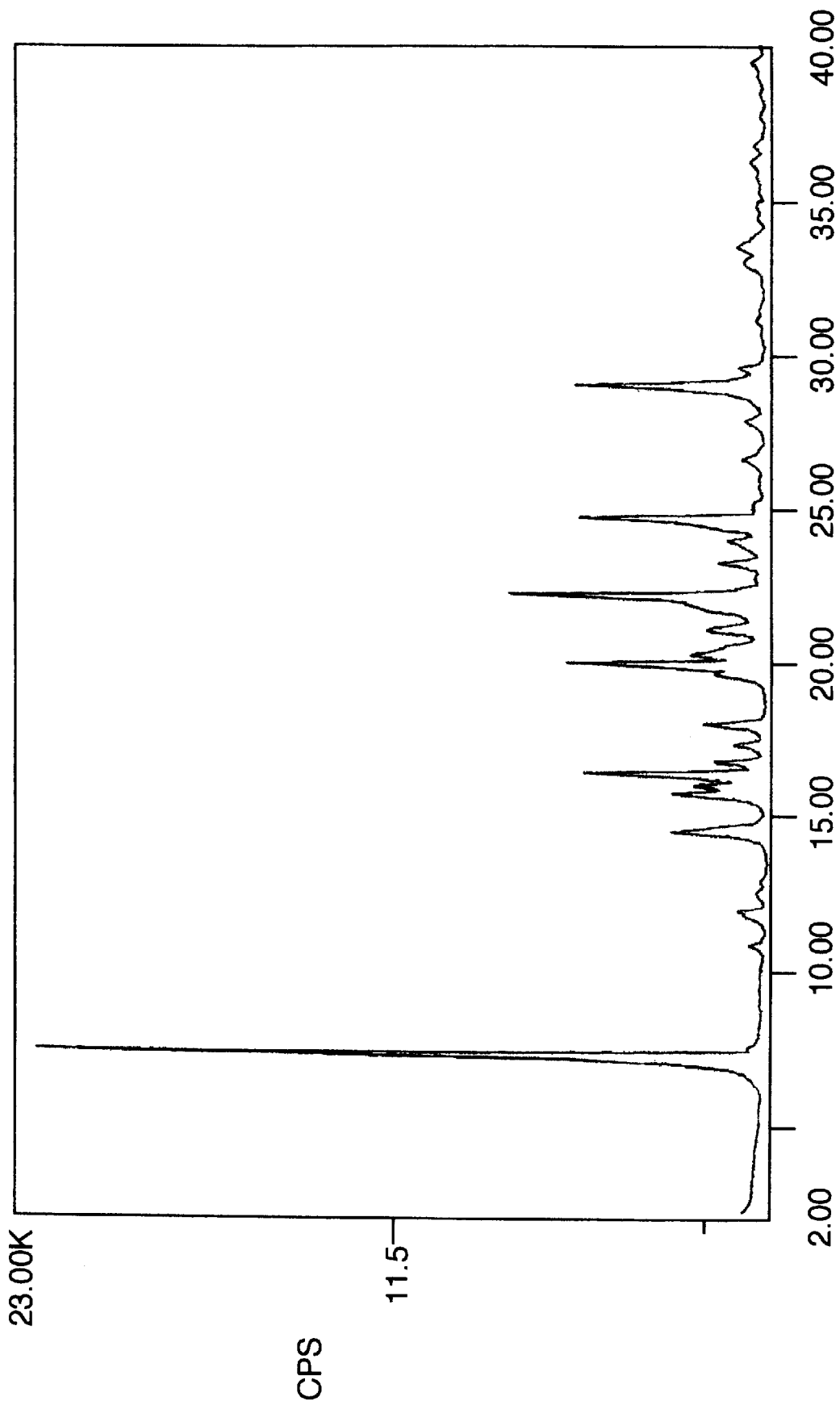
FIG. 1 shows the X-ray powder diffraction pattern obtained by Cu—Kα rays of the crystal of this invention obtained in Example 3. The abscissa and ordinate indicate diffraction angle and intensity, respectively.

BEST MODE FOR CARRYING OUT THE INVENTION 3,3'-Diallyl-4,41-dihydroxydiphenyl sulfone used in this invention is a crystal having DSC (Te) of at least 149° C., preferably at least 151.5° C. and more preferably at least 152° C. Incidentally, DSC (Te) means an extrapolated melt-initiating temperature (Te) in a differential scanning calorimeter. Incidentally, the DSC analysis conditions are such that aluminum crimp cell (P/N 201-52943) is used and the amount of sample is 5 mg. The temperature-elevating conditions are 10° C./min at up to 100° C. and 5° C./min at 100° C. or higher temperatures.

This crystal is preferably of a crystal form characterized by an X-ray diffraction pattern having at least peaks at diffraction angles (2θ) [°] of 7.2 and 22.0 obtained by an X-ray powder diffractometry using Cu—Kα rays, more particularly having, in addition to the peaks at diffraction angles (2θ) [0] of 7.2 and 22.0, relatively strong peaks at 14.5, 16.3, 18.0, 20.0, 21.0, 24.7 and 29.0. Incidentally, in the diffraction angle (2θ) [°], an error of about ±0.1 is tolerated.

Also, the measurement conditions in the X-ray powder diffractometry are as follows: Name of apparatus: RAD-2C (Rigaku Denki K. K.)

| Target: | Cu |
|---|---|
| Scanning angle: | 2°–40.0° |
| Scanning speed: | 2°/min |
| Tube voltage: | 40 KV |
| Tube current: | 30 mA |
| Slit: | DS 1, RS 0.15, SS 1 |

The purity of the crystal (di-rearrangement form) of 3,3'-diallyl-4,4'-dihydroxydiphenyl sulfone used in this invention is 95% or more, preferably 95.5% or more, more preferably 96% or more and much more preferably 97% or more. Moreover, in this crystal, as by-products, there are present monoallyl form (3-allyl-4,4'-dihydroxydiphenyl sulfone), indane form (5-(3-allyl-4-hydroxy)phenyl sulfone-1-oxa-2-methylindane), mono-rearrangement form (3-allyl- 4'-allyloxy-4-hydroxydiphenyl sulfone) and the like. The contents thereof are preferably such that the total amount of the above-mentioned three by-products is not more than 3% by the HPLC (high performance liquid chromatography) analysis, and it is more preferably not more than 2.5%, much more preferably not more than 2%. Moreover, it is preferable that the content of each of the three by-products is not more than 2%, and it is more preferable that the monoallyl form content is not more than 2%, the indane form content is not more than 1% and the mono-rearrangement form content is not more than 1%.

Here, the purity and content mean, respectively, purity and content based on the area ratio calculated from the chart obtained by the HPLC analysis (area %).
Incidentally, the conditions for the HPLC analysis are as follows:

| Analysis column: | Inertsil ODS-2 (4.6 mmφ × 25 cm) |
|---|---|
| Moving bed: | 65% methanol/water |
| Flow rate: | 0.6 ml/min |
| Column temperature: | 30° C. |
| Detector: | UV 254 nm |

Under the above conditions, a peak of about 14.4 min is of the di-rearrangement form, a peak of about 7.9 min is of the monoallyl form, a peak of about 17.7 min is of the indane form and a peak of about 22.3 min is of the mono-rearrangement form.

The crystal of 3,3'-diallyl-4,4'-dihydroxy-diphenyl sulfone of this invention is obtained by, for example, subjecting 4,4'-diallyloxydiphenyl sulfone to Claisen rearrangement reaction. For example, this rearrangement reaction is effected at 160–280° C., preferably 190–230° C., and more preferably 200–220° C. in an inactive, nonaqueous organic solvent having a high boiling point and completed when the amount of 3,3'-diallyl-4,4'-dihydroxydiphenyl sulfone produced, which is the di-rearrangement form, reaches about 90% (for example, 89 to 93%); the reaction product is extracted with an aqueous alkali solution and thereafter purified with activated carbon; subsequently, this extract is introduced into an aqueous acid solution (for example, dilute aqueous hydrogen chloride solution) at a high temperature to deposit crystals, or alternatively, the Claisen rearrangement reaction is effected in the same manner as mentioned above; thereafter the reaction product is extracted with an aqueous alkali solution; subsequently, water and a nonaqueous organic solvents (for example, an aromatic type organic solvent such as dichlorobenzene or the like) are added thereto; and an acidic aqueous solution (for example, an aqueous hydrogen chloride solution) is added until the neutralization equivalent becomes 40 to 60%; thereafter the water layer and the oil layer are separated; an acidic aqueous solution (for example, an aqueous hydrogen chloride solution) is further added to the water layer to deposit crystals. As the nonaqueous organic solvent used in the above reaction, there can be used without particular restriction all those which have a boiling point of at least 160° C., preferably at least 190° C., more preferably at least 200° C. and much more preferably 200 to 220° C. and are inactive to the starting compounds in this invention and their rearrangement products at the above-mentioned reaction temperatures. For example, a mixed solvent of an organic solvent of the aliphatic hydrocarbon type (e.g., MC Oil W-8 (manufactured by Idemitsu Kosan)) and kerosine (illuminating kerosine) is mentioned.

In the heat-sensitive recording material of this invention, a heat-sensitive color-developing layer is prepared by using, as the main components, a usually colorless or light-colored color former and crystals of 3,3'-diallyl-4,4'-dihydroxydiphenyl sulfone of this invention as a developer and, in addition, a sensitizer, a binder and, if necessary, a filler and other additives and the like, which are mentioned below. The amount of the crystals of 3,3'-diallyl-4,4'-dihydroxydiphenyl sulfone of this invention used is suitably 0.5 to 20 parts by weight, preferably 1 to 5 parts by weight, per part of the color former.

When the heat-sensitive color-developing layer is formed in this invention, the color former is used in a proportion of 1 to 50% by weight, preferably 5 to 30% by weight; the crystals of 3,3'-diallyl-4,4'-dihydroxydiphenyl sulfone of this invention are used in a proportion of 1 to 80% by weight, preferably 5 to 40% by weight; the sensitizer is used in a proportion of 0.5 to 80% by weight, preferably 5 to 40% by weight; the binder is used in a proportion of 1 to 90% by weight; the developer and sensitizer which can be used in combination are used each in a proportion of 0 to 40% by weight; the filler is used in a proportion of 0 to 80% by weight and other components such as lubricant, surface active agent, defoaming agent, ultraviolet absorber and the like are used each in any proportion, for example, each in a proportion of 0 to 30% by weight (% by weight is the weight ratio of each component in the heat-sensitive color-developing layer).

Examples of the color former which can be used may be those which are generally used in pressure-sensitive recording paper and heat-sensitive recording paper and are not particularly limited. As specific examples, there are mentioned fluorane type compounds, triarylmethane type compounds, spiro type compounds, diphenylmethane type compounds, thiazine type compounds, lactam type compounds, fluorene type compounds and the like.

As the fluorane type compound, there are mentioned 3-diethylamino-6-methyl-7-anilinofluorane, 3-dibutylamino-6-methyl-7-anilinofluorane, 3-(N-methyl-N-cyclohexylamino)-6-methyl-7-anilinofluorane, 3-(N-ethyl-N-isopentylamino)-6-methyl-7-anilinofluorane, 3-(N-ethyl-N-isobutylamino)-6-methyl-7-anilinofluorane, 3-[N-ethyl-N-(3-ethoxypropyl)amino]-6-methyl-7-anilinofluorane, 3-(N-ethyl-N-hexylamino)-6-methyl-7-anilinofluorane, 3-dipentylamino-6-methyl-7-anilinofluorane, 3-(N-methyl-N-propylamino)-6-methyl-7-anilinofluorane, 3-(N-ethyl-N-tetrahydrofuryl-amino)-6-methyl-7-anilinofluorane, 3-diethylamino-6-methyl-7-(p-chloroanilino)fluorane, 3-diethylamino-6-methyl-7-(p-fluoroanilino)fluorane, 3-[N-ethyl-N-(p-tolyl)amino]-6-methyl-7-anilinofluorane, 3-diethylamino-6-methyl-7-(p-toluidino)fluorane, 3-diethylamino-7-(o-chloroanilino)-fluorane, 3-dibutylamino-7-(o-chloroanilino)fluorane, 3-diethylamino-7-(o-fluoroanilino)fluorane, 3-dibutylamino-7-(o-fluoroanilino)fluorane, 3-diethylamino-7-(3,4-dichloroanilino)fluorane, 3-pyrrolidino-6-methyl-7-anilinofluorane, 3-diethylamino-6-chloro-7-ethoxyethylaminofluorane, 3-diethylamino-6-chloro-7-anilinofluorane, 3-diethylamino-7-chlorofluorane, 3-diethylamino-7-methylfluorane, 3-diethylamino-7-octylfluorane, 3-[N-ethyl-N-(p-tolyl)amino]-6-methyl-7-phenethylfluorane and the like.

As the triarylmethane type compound, there are mentioned, for example, 3,3-bis(p-dimethylaminophenyl)-6-dimethylaminophthalide (another name: crystal violet lactone or CVL), 3,3-bis(p-dimethylaminophenyl)phthalide, 3-(p-dimethylaminophenyl)-3-(1,2-dimethylaminoindol-3-yl)phthalide, 3-(p-dimethylaminophenyl)-3-(2-methylindol-3-yl)phthalide, 3-(p-dimethylaminophenyl)-3-(2- phenylindol-3-yl)phthalide, 3,3-bis(1,2-dimethylindol-3-yl)-5-dimethylaminophthalide, 3,3-bis(1,2-dimethylindol-3-yl)-6-dimethylaminophthalide, 3,3-bis(9-ethylcarbazol-3-yl)-5-dimethylaminophthalide, 3,3-(2-phenylindol-3-yl)-5-dimethylaminophthalide, 3-p-dimethylaminophenyl-3-(1-methylpyrrol-2-yl)-6-dimethylaminophthalide and the like.

As the spiro compound, there are mentioned, for example, 3-methylspirodinaphthopyran, 3-ethylspirodinaphthopyran, 3,3-dichlorospirodinaphthopyran, 3-benzylspirodinaphthopyran, 3-propylspirobenzopyran, 3-methylnaphtho-(3-methoxybenzo)spiropyran, 1,3,3-trimethyl-6-nitro-8'-methoxyspiro(indoline-2,2'-benzopyran) and the like. As the diphenylmethane type compound, there are mentioned, for example, N-halophenylleucoauramine, 4,4-bis-dimethylaminophenylbenzhydryl benzyl ether, N-2,4,5-trichlorophenylleucoauramine and the like. As the thiazine type compound, there are mentioned, for example, benzoyl Leucomethylene Blue, p-nitrobenzoyl Leucomethylene Blue, and the like. As the lactam type compound, there are mentioned, for example, Rhodamine B anilinolactam, Rhodamine B p-chloroanilinolactam and the like. As the fluorene type compound, there are mentioned, for example, 3,6-bis(dimethylamino)fluorenespiro(9,3')-6'-dimethylaminophthalide, 3,6-bis(dimethylamino)fluorenespiro(9,3')-6'-pyrrolidinophthalide, 3-dimethylamino-6-diethylamino-fluorenesprio(9,3')-6'-pyrrolidinophthalide and the like. These color-developable compounds are used alone or in admixture.

As the sensitizer which can be used, there can be used those which are solid at ordinary temperature and have a melting point of not less than about 70° C., for example, waxes such as animal and vegetable waxes, synthetic waxes and the like; higher fatty acids; higher fatty acid amides; higher fatty acid anilides; acetylated aromatic amines; naphthalene derivatives; aromatic ethers; aromatic carboxylic acid derivatives; aromatic sulfonic acid ester derivatives; carbonic or oxalic acid diester derivatives; biphenyl derivatives; terphenyl derivatives; and the like.

As the waxes, there are mentioned, for example, Japan wax, carnauba wax, shellac, paraffin, montan wax, oxidized paraffin, polyethylene wax, polyethylene oxide and the like. As the higher fatty acids, there are mentioned, for example, stearic acid, behenic acid and the like. As the higher fatty acid amides, there are mentioned, for example, stearic acid amide, oleic acid amide, N-methylstearic acid amide, erucic acid amide, methylol-behenic acid amide, methylenebisstearic acid amide, ethylenebisstearic acid amide and the like. As the higher fatty acid anilides, there are mentioned, for example, stearic acid anilide, linoleic acid anilide and the like.

As the acetylated aromatic amines, there are mentioned, for example, acetotoluidide and the like. As the naphthalene derivatives, there are mentioned, for example, 1-benzyloxynaphthalene, 2-benzyloxynaphthalene, phenyl 1-hydroxynaphthoate and the like. As the aromatic ethers, there are mentioned, for example, 1,2-diphenoxyethane, 1,4-diphenoxybutane, 1,2-bis(3-methylphenoxy)ethane, 1,2-bis(4-methoxyphenoxy)ethane, 1,2-bis(3,4-dimethylphenyl)ethane, 1-phenoxy-2-(4-chlorophenoxy) ethane, 1-phenoxy-2-(4-methoxyphenoxy)ethane and the like.

As the aromatic carboxylic acid derivatives, there are mentioned, for example, benzyl p-hydroxybenzoate, benzyl p-benzyloxybenzoate, dibenzyl terephthalate and the like. As the aromatic sulfonic acid ester derivatives, there are mentioned, for example, phenyl p-toluene sulfonate, phenyl mesitylenesulfonate, 4-methylphenyl mesitylenesulfonate and the like. As the carbonic or oxalic acid diester derivative, there are mentioned, for example, diphenyl carbonate, dibenzyl oxalate, di-(4-chlorobenzyl) oxalate and the like. As the biphenyl derivatives, there are mentioned, for example, p-allyloxybiphenyl and the like. As the terphenyl derivatives, there are mentioned, for example, m-terphenyl (1,3-diphenylbenzene) and the like.

As the binder which can be used, there are used, water soluble materials such as, for example, methyl cellulose, methoxy cellulose, hydroxyethyl cellulose, carboxymethyl cellulose, sodium carboxymethyl cellulose, cellulose, polyvinyl alcohol (PVA), carboxyl group-modified polyvinyl alcohol, sulfonic acid group-modified polyvinyl alcohol, polyvinylpyrrolidone, polyacrylamide, polyacrylic acid, starch and their derivatives, casein, gelatine, water-soluble isoprene rubber, alkali salts of styrene/maleic anhydride copolymer, alkali salts of iso- (or diiso) butylene/maleic anhydride copolymer and the like; or hydrophobic polymer emulsions such as polyvinyl acetate, vinyl chloride/vinyl acetate copolymer, polystyrene, polyacrylic acid esters, polyurethane, styrene/butadiene (BS) copolymer, carboxylated styrene/butadiene (SB) copolymer, styrene/butadiene/acrylic acid copolymer, complex particles of colloidal silica and acrylic resin and the like; etc.

As the filler which can be used, there are mentioned, for example, calcium carbonate, magnesium carbonate, magnesium oxide, silica, white carbon, talc, clay, alumina, magnesium hydroxide, aluminum hydroxide, aluminum oxide, barium sulfate, polystyrene resin, ureaformaldehyde resin and the like.

As the additives which can be used, there are, if necessary, added, for example, metal salts of higher fatty acids such as zinc stearate, calcium stearate and the like for the purpose of prevention of thermal head abrasion, prevention of sticking and the like; phenol derivatives which impart an oxidization-preventing or age-preventing effect; ultraviolet absorbers of benzophenone type, benzotriazole type and the like; various surface active agents; defoaming agents; and the like. As the ultraviolet absorbers which can be used, there are mentioned, for example, 2-(2'-hydroxy-5'-methylphenyl) benzotriazole, 2-(2'-hydroxy-3',5'-di-t-butylphenyl)-5-chlorobenzotriazole, 2-(2'-hydroxy-3'-t-butyl-5'-methylphenyl)-5-chlorobenzotriazole, 2-(2'-hydroxy-5'-t-octylphenyl)benzo-triazole, 2-(2'-hydroxy-5'-t-octoxyphenyl)benzotriazole, 2-(2'-hydroxy-3',5'-di-t-butylphenyl )-5-chlorobenzotriazole, 2-(2'-hydroxy-3',5'-di-t-amylphenyl)-5-chlorobenzotriazole and the like.

The heat-sensitive recording material of this invention is prepared by using the above-mentioned materials by, for example, the following method. That is to say, first of all, according to the conventional procedure, each of the color former, the 3,3'-diallyl-4,4'-dihydroxydiphenyl sulfone of this invention and the sensitizer is separately pulverized and dispersed together with the binder or, if necessary, other additives and the like in a dispersing machine such as a ball mill, an atomizer, a sand mill or the like, thereafter (when the pulverization and dispersion are effected by a wet method, water is usually used as a medium) they are mixed to prepare a coating solution for the heat-sensitive color-developing layer, and this is then coated on a support such as paper, a plastic sheet, a synthetic paper or the like usually in a proportion of 1 to 20 g/m$^2$ by dry weight by means of a bar coater, a blade coater or the like (the ratio of the color former to the developer is usually 1:1 to 1:10 by dry weight) and then dried to obtain the heat-sensitive recording material of this invention. Moreover, if necessary, an intermediate layer may be provided between the heat-sensitive color-developing layer and the support or an overcoat layer may be provided on the heat-sensitive color-developing layer.

This invention is explained more specifically by Examples; however, this invention should not be construed to be limited thereto. In the Examples, the term "part" means part by weight.

EXAMPLE 1

Preparation of Crystal of 3,3'-diallyl-4,4'-dihydroxydiphenyl sulfone)

Into 220 parts of MC Oil w-8 (manufactured by Idemitsu Kosan) and 176.7 parts of illuminating kerosine (manufactured by NIPPON OIL) was charged 330 parts of 4,4'-diallyloxydiphenyl sulfone and the resulting mixture was heated at 202° C. for 7 hours under a nitrogen gas stream to effect rearrangement reaction. The content of each component in the reaction product at that time based on the area ratio determined by the HPLC analysis was as follows: di-rearrangement form: 90.5%, unreacted materials: not more than 0.1%, monoallyl form: 1.3%, mono-rearrangement form: 3.6% and indane form: 1.4%. To this reaction liquid was added 43.3 parts of illuminating kerosine and thereafter the resulting mixture was cooled, after which 577.5 parts of 14.3% sodium hydroxide solution was added and the mixture was stirred for 1 hour and then allowed to stand. Subsequently, the water layer portion was taken out and 559.64 parts of 8.2% aqueous hydrogen chloride solution was added thereto, after which the temperature was elevated to 80–85° C. Subsequently, 49.5 parts of activated carbon powder was added, and then the resulting mixture was stirred at the same temperature for 1 hour. The mixture was filtered for removing the activated carbon, and the filtrate was dropwise added gradually to 700 parts of a previously prepared 10.4% aqueous hydrogen chloride solution at 80–85° C. with stirring to deposit crystals. The crystals were separated by filtration, sufficiently washed with warm water until it became neutral and then dried to obtain 157 parts of crystals.

DSC (Te) of the crystals obtained was 155.8° C. The results of HPLC analysis were as follows: direarrangement form: 96.4%, unreacted materials: not more than 0.1%, monoallyl form: 1.6%, mono-rearrangement form: 0.8% and indane form: 0.3%. Moreover, the crystals were subjected to X-ray powder diffraction measurement using Cu—Kα rays to find, in addition to peaks at diffraction angles (2θ) [0] of 7.2 and 22.0, relatively strong peaks at 14.5, 16.3, 18.0, 20.0, 21.0, 24.7 and 29.0, and this diffraction pattern was the same as that of the crystals obtained by the method of Example 3. These results were collected in Table 2.

EXAMPLE 2

Production of Heat-Sensitive Recording Material

Each of the mixtures having the following compositions was pulverized and dispersed using a sand grinder for 1 hour to prepare each of the Liquid [A], Liquid [B] and Liquid [C].

| Liquid [A]: | 3-Dibutylamino-6-methyl-7-anilino-fluorane | 25 parts |
| | 25% Aqueous PVA solution | 20 parts |
| | Water | 55 parts |
| Liquid [B]: | 3,3'-Diallyl-4,4'-dihydroxydiphenyl | 30 parts |

-continued

| | sulfone obtained in Example 1 | |
| | 25% Aqueous PVA solution | 20 parts |
| | Water | 50 parts |
| Liquid [C]: | m-Terphenyl (manufactured by Nippon Steel Chemical) | 25 parts |
| | 25% Aqueous PVA solution | 20 parts |
| | Water | 55 parts |

Subsequently, they were mixed in the following proportion to prepare a coating solution for heat-sensitive color-developing layer:

| Liquid [A] | 1.5 parts |
| Liquid [B] | 2.0 parts |
| Liquid [C] | 3.5 parts |
| Water | 3.0 parts. |

The above coating solution for heat-sensitive color-developing layer was coated on a support (neutralized paper) so that the dry weight became 4.6 g/m$^2$ and then dried at 50–55° C. for 5 minutes to produce the heat-sensitive recording material of this invention.

Developed Color Density Test

Using a tester of Toyo Seiki Heat Gradient HG-100, the obtained heat-sensitive recording material of this invention was developed (developing conditions: a pressure of 1.0 Kg/m$^2$ was applied for 5 seconds at 130° C.). The image density obtained by the development was measured by a Macbeth reflection densitometer Model RD-914. As a result, the developed color density was 1.30. Incidentally, the ground density (a color density of the ground) was 0.06. The developed color density means that the larger the value, the higher the degree of color development. Contrarily, it means that the lower the value, the lower the degree of color development and the less the ground color change.

Resistance Test under Heat and Moisture)

The above coating solution for heat-sensitive color-developing layer was coated on a support (neutralized paper) so that the wet weight became 21 g/m$^2$ (dry weight: 4.6 g/m$^2$), and immediately thereafter, subjected to a heat and moisture resistance tester (test conditions: 70° C., 95% RH, 5 minutes) and then to measurement by a Macbeth reflection densitometer model RD-914. As a result, the ground density (a color density of the ground) was 0.16. The results were collected in Table 1.

EXAMPLE 3

Preparation of Crystal of 3,31-diallyl-4,41-dihydroxydiphenyl Sulfone)

Into 160 parts of MC Oil W-8 (manufactured by Idemitsu Kosan) and 128.5 parts of illuminating kerosine (manufactured by NIPPON OIL) was charged 240 parts of 4,4'-diallyloxydiphenyl sulfone, and the mixture was heated at 202° C. for 9 hours under a nitrogen gas stream to be subjected to rearrangement reaction. The content of each component in the reaction product at that time based on the area ratio determined by the HPLC analysis was as follows: di-arrangement form: 92.7%, unreacted materials: not more than 0.1%, monoallyl form: 1.1%, mono-rearrangement form: 1.6% and indane form: 1.8%. To this reaction liquid was added 31.5 parts of illuminating kerosine and thereafter the mixture was cooled, after which 300 parts of 20% sodium hydroxide solution and 120 parts of water were added. The resulting mixture was stirred for 1 hour and then allowed to stand sufficiently until it separated into two layers. Subsequently, the water layer portion was taken out and 100 parts of water and 120 parts of orthodichlorobenzene were added thereto, after which the temperature was elevated to 70° C., and then 184 parts of 18% aqueous hydrogen chloride solution was added (neutralization equivalent: 43%). The resulting mixture was stirred at the same temperature for 2 hours and then allowed to stand sufficiently. The water layer (upper layer) was taken out and 36 parts of activated carbon powder was added, after which the resulting mixture was stirred for 1 hour. The mixture was filtered for removing the activated carbon, and the filtrate was neutralized with 152 parts of 18% aqueous hydrogen chloride solution to produce crystals. The crystals produced were separated by filtration and dried to obtain 45.6 parts of crystals of 3,3'-diallyl-4,4'-dihydroxydiphenyl sulfone.

DSC (Te) of the crystals obtained was 155.0° C. The HPLC analysis results were as follows: di-rearrangement form: 96.4%, unreacted materials: not more than 0.1%, monoallyl form: 1.5%, one-side rearrangement form: not more than 0.1% and indane form: 0.3%. Moreover, the crystals were subjected to X-ray powder diffraction measurement using Cu—Kα rays to find, in addition to peaks at diffraction angles (2θ) [°] of 7.2 and 22.0, relatively strong peaks at 14.5, 16.3, 18.0, 20.0, 21.0, 24.7 and 29.0. This crystal form is called α form. This X-ray diffraction pattern is shown in FIG. 1. These results were collected in Table 2.

EXAMPLE 4

Production of Heat-Sensitive Recording Material

Each of the mixtures having the following compositions was pulverized and dispersed using a sand grinder for 1 hour to prepare each of Liquid [A], Liquid [B] and Liquid [C].

| Liquid [A]: | 3-Dibutylamino-6-methyl-7-anilino-fluorane | 25 parts |
|---|---|---|
| | 25% Aqueous PVA solution | 20 parts |
| | Water | 55 parts |
| Liquid [B]: | 3,3'-Diallyl-4,4'-dihydroxydiphenyl sulfone obtained in Example 1 | 30 parts |
| | 25% Aqueous PVA solution | 20 parts |
| | Water | 50 parts |
| Liquid [C]: | m-Terphenyl (manufactured by Nippon Steel Chemical) | 25 parts |
| | 25% Aqueous PVA solution | 20 parts |
| | Water | 55 parts |

Subsequently, they were mixed in the following proportion to prepare a coating solution for heat-sensitive color-developing layer:

| Liquid [A] | 1.5 parts |
|---|---|
| Liquid [B] | 2.0 parts |
| Liquid [C] | 3.5 parts |
| Water | 3.0 parts. |

The above coating solution for heat-sensitive color-developing layer was coated on a support (neutralized paper) so that the dry weight became 4.6 g/m² and then dried at 50–55° C. for 5 minutes to produce the heat-sensitive recording material of this invention.

Developed Color Density Test

Using a tester of Toyo Seiki Heat Gradient HG-100, the obtained heat-sensitive recording material of this invention was developed (developing conditions: a pressure of 1.0 Kg/m² was applied for 5 seconds at 130° C.). The image density obtained by the development was measured by a Macbeth reflection densitometer Model RD-914. As a result, the developed color density was 1.30. Incidentally, the ground density (a color density of the ground) was 0.05.

Resistance Test under Heat and Moisture

The above coating solution for heat-sensitive color-developing layer was coated on a support (neutralized paper) so that the wet weight became 21 g/m (dry weight: 4.6 g/m²), and immediately thereafter, subjected to a heat and moisture resistance tester (test conditions: 70° C., 95% RH, 5 minutes) and then to measurement by a Macbeth reflection densitometer Model RD-914. As a result, the ground density (a color density of the ground) was 0.09. The results were collected in Table 1.

COMPARATIVE EXAMPLE 1

In accordance with the Example 1 stated in JP-A-61-89, 090, crystals of 3,3'-diallyl-4,4'-dihydroxydiphenyl sulfone were prepared. That is to say, 250 parts of 4,4'-diallyloxydiphenyl sulfone was subjected to thermal rearrangement at 195–210° C. for 6 hours under a nitrogen gas stream to obtain 238 parts of crystals of 3,3'-diallyl-4,4'-dihydroxydiphenyl sulfone. DSC (Te) of the product was 145.8° C. The HPLC analysis results were as follows: di-rearrangement form: 89.7%, unreacted materials: 0.3%, monoallyl form: 1.3%, mono-rearrangement form: not more than 4.4% and indane form: 1.1%. In addition, the X-ray powder diffraction measurement was conducted using Cu—Kα rays to find relatively strong peaks at diffraction angles (2θ) [°] of 7.04, 10.85, 14.14, 15.78, 17.51 and 22.98, and the crystals had a diffraction pattern different from that of the crystals obtained by the methods of Examples 1 and 3 of this invention. This crystal form is called β form.

Figure 2:
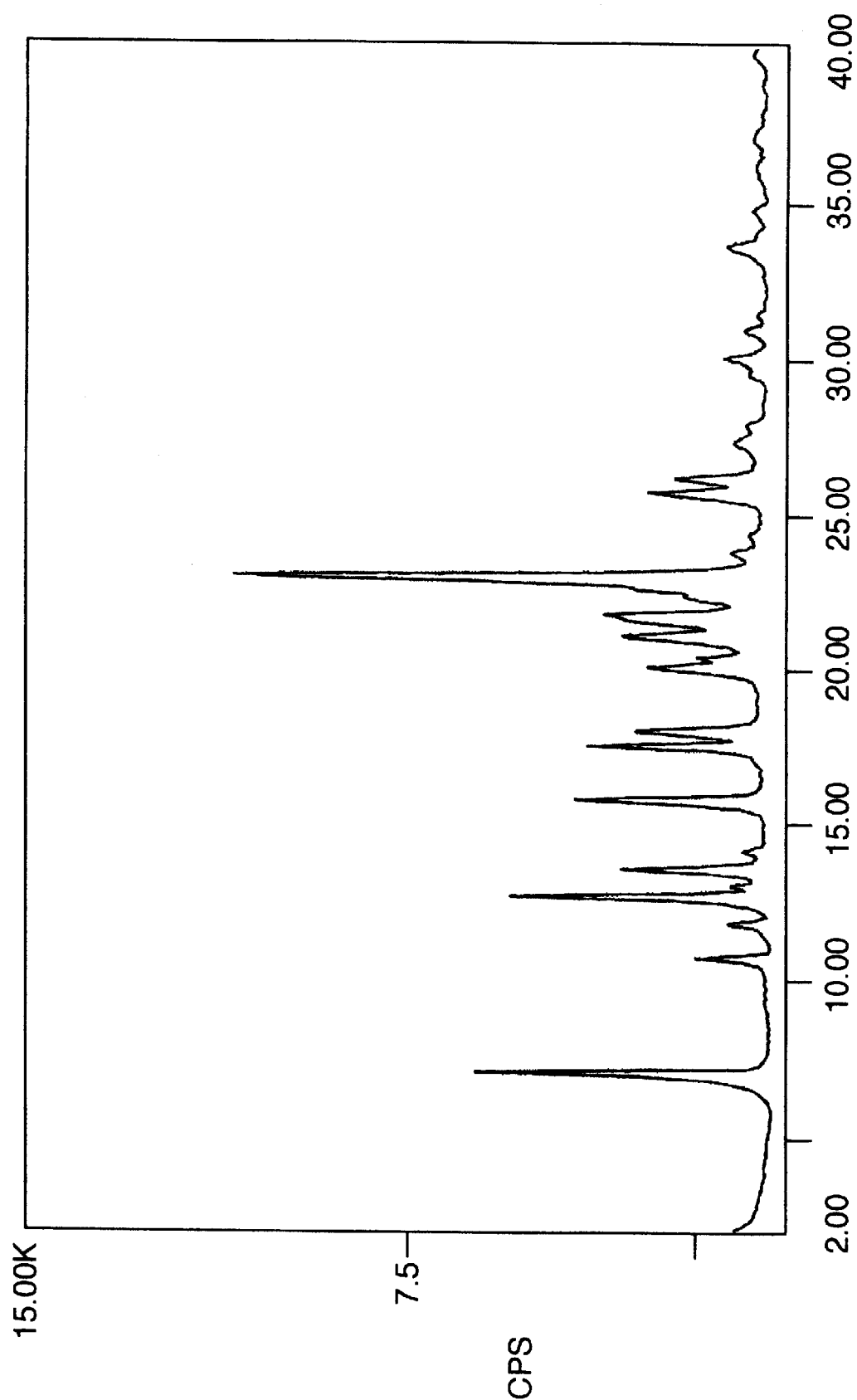
FIG. 2 shows the X-ray powder diffraction pattern obtained by Cu—Kα rays of the crystal obtained in Comparative Example 1. The abscissa and ordinate indicate diffraction angle and intensity, respectively.

This X-ray diffraction pattern is shown in FIG. 2. These results were collected in Table 2.

Using the above crystals, a heat-sensitive recording paper was prepared in the same manner as in Example 4 of this invention and subjected to the resistance test under heat and moisture. The results are shown in Table 1.

COMPARATIVE EXAMPLE 2

In accordance with the Example 3 stated in JP-A-62-53, 957, crystals of 3,3'-diallyl-4,4'-dihydroxydiphenyl sulfone were prepared. That is to say, 330 parts of 4,4'-diallyloxydiphenyl sulfone was charged into 220 parts of MC Oil W-8 (manufactured by Idemitsu Kosan) and 176.7 parts of illuminating kerosine (manufactured by NIPPON OIL) and they were subjected to reaction at 202° C. for about 6 hours under a nitrogen gas stream. The content of each component in the reaction product at that time based on the area ratio determined by the HPLC analysis was as follows: diarrangement form: 84.1%, unreacted materials: 0.6%, monoallyl form: 1.1%, mono-rearrangement form: 11.8%, and the indane form: 0.8%. To this reaction liquid was added 43.3 parts of illuminating kerosine and thereafter 16.5 parts of ethylene glycol was added at 150° C. with stirring, after which an aqueous solution composed of 82.5 parts of sodium hydroxide and 495 parts of water was gradually added from 125° C. to form an alkaline aqueous solution of the reaction product. After allowing it to stand, the alkaline aqueous solution of the lower layer was taken out while the paraffin oil of the upper layer was left. Incidentally, the amount of illuminating kerosine used at the time of reaction is smaller than the amount of illuminating kerosine used as stated in the Example 3 of JP-A-62-53,957. This is because in the amount of illuminating kerosine used as stated in said Example 3, the temperature was able to be elevated only up to 195–197° C. and the reaction at 200–210° C. as stated in said Example 3 was unable to be conducted.

To this alkaline aqueous solution was added 320 parts of dichloroethane, and then, 388 parts of 20% aqueous hydrogen chloride solution was gradually added with stirring to acidify the solution, after which the solution was stirred at about 75° C. for a while and thereafter allowed to stand to separate into two layers. The aqueous inorganic salt solution of the upper layer was withdrawn and to the residue were added 320 parts of toluene and 33.6 parts of isopropanol, after which the resulting mixture was stirred at 80–85° C. for a while to form a solution. Thereafter, the solution was cooled to deposit crystals. The crystals were collected by filtration at 25° C., washed with a mixed solution of 160 parts of dichloroethane and 160 parts of toluene and successively with 400 parts of water and thereafter dried to obtain 166.4 parts of crystals (yield: 50.4%).

DSC (Te) of the crystals obtained was 146.4° C. The HPLC analysis results were as follows: direarrangement form: 95.4%, unreacted materials: not more than 0.1%, monoallyl form: 0.6%, mono-rearrangement form: 2.8% and the indane form: 0.2%. In addition, the X-ray powder diffraction measurement was conducted using Cu—Kα rays to find that the diffraction pattern was the same as that of the crystals obtained by the methods of Examples 1 and 3 of this invention. These results were collected in Table 2.

Using the above crystals, a heat-sensitive recording paper was prepared in the same manner as in Example 4 of this invention and subjected to the resistance test under heat and moisture. The results obtained are shown in Table 1.

TABLE 1

|  | Resistance test under heat and moisture Ground density |
| --- | --- |
| Example 2 | 0.16 |
| Example 4 | 0.09 |
| Comparative Example 1 | 1.15 |
| Comparative Example 2 | 0.27 |

As is clear from Table 1, in Comparative Example 1, the ground density in the resistance test under heat and moisture is as large as 1.15 and hence color development takes place. In addition, in Comparative Example 2, the ground density was 0.27. On the other hand, in the case of the heat-sensitive recording material of this invention, the ground density in the resistance test under heat and moisture is 0.16 in Example 2 and 0.09 in Example 4. This means that the color development has been inhibited about 40% in Example 2 and about 66% in Example 4 as compared with Comparative Example 2, and hence, it is seen that the heat-sensitive recording material of this invention is less in change of the ground color than in the Comparative Examples.

TABLE 2

|  | Example No. | | Comp. Ex. No. | |
| --- | --- | --- | --- | --- |
|  | 1 | 3 | 1 | 2 |
| DSC (Te: ° C.) | 155.8 | 155.0 | 145.8 | 146.4 |
| Crystal form | α | α | β | α |
| Main compound content (%) | 96.4 | 98.2 | 89.7 | 95.4 |
| Unreacted material content (%) | 0.1or less | 0.1or less | 0.3 | 0.1or less |
| Mono-form content (%) | 1.6 | 1.5 | 1.3 | 0.6 |
| One-side re-arrangement form content (%) | 0.8 | 0.1or less | 4.4 | 2.8 |
| Indane form content (%) | 0.3 | 0.3 | 1.1 | 0.2 |
| Total by-product content (%) | 2.7 | 1.9or less | 6.8 | 3.6 |

Note: The total by-product content (%) means the total of the contents of three of monoallyl form, mono-rearragement form and indane form in the crystal.

As is clear from Table 2, the crystal in Comparative Example 1 and the crystal used in this invention are greatly different in crystal form and Te value of DSC and also in total by-product content, particularly mono-rearrangement form content and indane form content. The crystal in Comparative Example 2 and, the crystal used in this invention are greatly different in Te value of DSC and also in total by-product content, particularly mono-rearrangement form content.

INDUSTRIAL APPLICABILITY

A heat-sensitive recording material obtained using the novel crystal of bisphenol s derivative of this invention (3,3'-diallyl-4,4'-dihydroxydiphenyl sulfone) is high in sensitivity and little in the discoloration of the ground in heat and moisture, excellent in image durability and high in industrial applicability.

What is claimed is:

1. A heat-sensitive recording material which has, on a support, a heat-sensitive color-developing layer comprising a usually colorless or light-colored color former and a developer capable of developing the color former upon heating, characterized by containing, as the developer, crystals of 3,3'-diallyl-4,4'-dihydroxydiphenyl sulfone which have DSC (Te) of at least 149° C. and are of a crystal form characterized by an X-ray diffraction pattern having peaks at least at diffraction angles (2θ) [°] of 7.2 and 22.0, obtained by an X-ray powder diffractometry using Cu—Kα rays.

2. The heat-sensitive recording material according to claim 1, wherein the DSC (Te) of the crystal of 3,3'-diallyl-4,4'-dihydroxydiphenyl sulfone is at least 151.5° C.

3. The heat-sensitive recording material according to claim 1, wherein the crystal of 3,3'-diallyl-4,4'-dihydroxydiphenyl sulfone is of a crystal form characterized by an X-ray diffraction pattern having, in addition to peaks at diffraction angles (2θ) [°] of 7.1 and 22.0, peaks at 14.5, 16.3, 18.0, 20.0, 21.0, 24.7 and 29.0, obtained by an X-ray powder diffractometry using Cu—Kα rays.

4. The heat-sensitive recording material according to claim 1, wherein the 3,3'-diallyl-4,4l-dihydroxydiphenyl sulfone content in the crystals of 3,3'-diallyl-4,4l-dihydroxydiphenyl sulfone is at least 95%.

5. The heat-sensitive recording material according to claim 1, wherein the 3,3'-diallyl-4,4'-dihydroxydiphenyl sulfone content in the crystals of 3,3'-diallyl-4,4'-dihydroxydiphenyl sulfone is at least 95.5%.

6. The heat-sensitive recording material according to claim 1, wherein the total of the three contents of 3-allyl-4,4'-dihydroxydiphenyl sulfone, 5-(3-allyl-4-hydroxy) phenyl sulfone-1-oxa-2-methylindane and 3-allyl-4'-allyloxy-4-hydroxydiphenyl sulfone in the crystals of 3,3'-diallyl-4,4'-dihydroxydiphenyl sulfone is not more than 3%.

7. The heat-sensitive recording material according to claim 6, wherein the 3-allyl-4,4'-dihydroxydiphenyl sulfone content in the crystals of 3,3'-diallyl-4,4'-dihydroxydiphenyl sulfone is not more than 2%.

8. The heat-sensitive recording material according to claim 1, wherein the total of the three contents of 3-allyl-4,4'-dihydroxydiphenyl sulfone, 5-(3-allyl-4-hydroxy) phenyl sulfone-1-oxa-2-methylindane and 3-allyl-4'-allyloxy-4-hydroxydiphenyl sulfone in the crystals of 3,3'-diallyl-4,4'-dihydroxydiphenyl sulfone is not more than 2%.

9. A heat-sensitive recording material in which a heat-sensitive color-developing layer comprising, as the main components, a usually colorless or light-colored color former and a developer capable of developing the color former upon heating is provided on a support, characterized by comprising, as the developer, crystals of 3,3'-diallyl-4,4'-dihydroxydiphenyl sulfone having the following features (a) to (e):

(a) the DSC (Te) is at least 149° C., (b) the crystal is of a crystal form characterized by an X-ray diffraction pattern having peaks at diffraction angles (2θ) [0] of 7.2 and 22.0, obtained by an X-ray powder diffractometry using Cu—Kα rays, (c) the 3,3'-diallyl-4,4'-dihydroxydiphenyl sulfone content is at least 95.5%, (d) the total of the three contents of 3-allyl-4,4'-dihydroxydiphenyl sulfone, 5-(3-allyl-4-hydroxy) phenyl sulfone-1-oxa-2-methylindane and 3-allyl-4'-allyloxy-4-hydroxydiphenyl sulfone is not more than 3%, and (e) the 3-allyl-4,4'-dihydroxydiphenyl sulfone content is not more than 2%, the 5-(3-allyl-4-hydroxy)phenyl sulfone-1-oxa-2-methylindane content is not more than 2% and the 3-allyl-4'-allyloxy-4-hydroxydiphenyl sulfone content is not more than 2%.

10. A heat-sensitive recording material which has, on a support, a heat-sensitive color-developing layer comprising a usually colorless or light-colored color former and a developer capable of developing the color former upon heating, characterized by containing, as the developer, crystals of 3,3'-diallyl-4,4'-dihydroxydiphenyl sulfone having the following features (f) to (j):

(f) the DSC (Te) is at least 151.5° C., (g) the crystal is of a crystal form characterized by an X-ray diffraction pattern having, in addition to peaks at diffraction angles (2θ) [°] of 7.2 and 22.0, peaks at 14.5, 16.3, 18.0, 20.0, 21.0, 24.7 and 29.0, obtained by an X-ray powder diffractometry using Cu—Kα rays, (h) the 3,3'-diallyl-4,41-dihydroxydiphenyl sulfone content is at least 96%, (i) the total of the three contents of 3-allyl-4,4'-dihydroxydiphenyl sulfone, 5-(3-allyl-4-hydroxy) phenyl sulfone-1-oxa-2-methylindane and 3-allyl-4'-allyloxy-4-hydroxydiphenyl sulfone is not more than 2%, and (j) the 3-allyl-4,4'-dihydroxydiphenyl sulfone content is not more than 2%, the 5-(3-allyl-4-hydroxy)-phenyl sulfone-1-oxa-2-methylindane content is not more than 1% and the 3-allyl-4'-allyloxy-4-hydroxydiphenyl sulfone content is not more than 1%.

11. A crystal of 3,3'-diallyl-4,4'-dihydroxydiphenyl sulfone which has an extrapolated melt-initiating temperature Te of DSC of at least 149° C. and which is of a crystal form characterized by an X-ray diffraction pattern having peaks at diffraction angles (2θ) [°] of 7.2 and 22.0, obtained by an X-ray powder diffractometry using cu—Kα rays.

12. The crystal of 3,3'-diallyl-4,41-dihydroxydiphenyl sulfone according to claim 11, wherein the 3,3'-diallyl-4,4'-dihydroxydiphenyl sulfone content is at least 95.5% and the total of the three contents of 3-allyl4,4'-dihydroxydiphenyl sulfone, 5-(3-allyl-4-hydroxy)phenyl sulfone-1-oxa-2-methylindane and 3-allyl-4'-allyloxy-4-hydroxydiphenyl sulfone is not more than 3%.

13. The crystal of 3,3'-diallyl-4,4'-dihydroxydiphenyl sulfone according to claim 12, wherein the 3-allyl-4,4'-dihydroxydiphenyl sulfone content is not more than 2%, the 5-(3-allyl-4-hydroxy)phenyl sulfone-1-oxa-2-methylindane content is not more than 2% and the 3-allyl-4'-allyloxy-4-hydroxydiphenyl sulfone content is not more than 2%.

14. The crystal of 3,3'-diallyl-4,4'-dihydroxydiphenyl sulfone according to claim 12, wherein the 3-allyl-4,4'-dihydroxydiphenyl sulfone content is not more than 2%, the 5-(3-allyl-4-hydroxy)phenyl sulfone-1-oxa-2-methylindane content is not more than 1%, the 3-allyl-4'-allyloxy-4-hydroxydiphenyl sulfone content is not more than 1%, and the total of the three contents is not more than 2%.

\* \* \* \* \*